United States Patent
Borrmann et al.

(10) Patent No.: US 11,826,283 B2
(45) Date of Patent: Nov. 28, 2023

(54) APPARATUS FOR INFLUENCING AN INTRAOCULAR PRESSURE

(71) Applicant: Carl Zeiss Meditec AG, Jena (DE)

(72) Inventors: Bernd Borrmann, Zoellnitz (DE); Martin Hacker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 418 days.

(21) Appl. No.: 16/780,787

(22) Filed: Feb. 3, 2020

(65) Prior Publication Data

US 2020/0170839 A1 Jun. 4, 2020

Related U.S. Application Data

(63) Continuation of application No. PCT/EP2018/071151, filed on Aug. 3, 2018.

(30) Foreign Application Priority Data

Aug. 3, 2017 (DE) ...................... 10 2017 117 657.8

(51) Int. Cl.
*A61F 9/007* (2006.01)
*A61F 9/00* (2006.01)
(Continued)

(52) U.S. Cl.
CPC ........ *A61F 9/00781* (2013.01); *A61F 9/0017* (2013.01); *A61B 3/16* (2013.01);
(Continued)

(58) Field of Classification Search
CPC .......... A61F 9/00781; A61F 2250/0013; A61F 9/0017; A61B 3/16; A61B 5/031;
(Continued)

(56) References Cited

U.S. PATENT DOCUMENTS 5,763,491 A * 6/1998 Brandt ................. A61K 31/196
514/603
5,810,005 A * 9/1998 Dublin, Jr. ............. A61B 5/021
600/398

(Continued)

FOREIGN PATENT DOCUMENTS

WO 2007127305 A2 11/2007
WO WO-2007127305 A2 * 11/2007 ............... A61B 3/16
(Continued)

OTHER PUBLICATIONS

Herbowski L. The major influence of the atmosphere on intracranial pressure: an observational study. Int J Biometeorol. Jan. 2017; 61(1):181-188. doi: 10.1007/s00484-016-1202-3. Epub Jun. 22, 2016. PMID: 27333899.*

(Continued)

*Primary Examiner* — Susan S Su
*Assistant Examiner* — Ted Yang
(74) *Attorney, Agent, or Firm* — Ewers IP Law PLLC; Falk Ewers

(57) ABSTRACT

An apparatus for influencing an intraocular pressure (IOP) of an eye with a controllable discharge device which is configured to discharge a liquid from at least one area of the eye. The apparatus includes a first sensor device which captures at least one first value that is characteristic for the IOP of the eye, and a second sensor device, which captures at least one second value that is characteristic for a pressure acting on the eye, and a control device which controls the discharge device at least at times taking account of the first characteristic value and the second characteristic value, wherein the second characteristic value is characteristic for an intracranial pressure and/or cerebrospinal pressure.

14 Claims, 2 Drawing Sheets

(51) Int. Cl.
*A61B 3/16* (2006.01)
*A61B 17/00* (2006.01)
*A61B 5/03* (2006.01)

(52) U.S. Cl.
CPC ..... *A61B 5/031* (2013.01); *A61B 2017/00022* (2013.01); *A61F 2250/0002* (2013.01); *A61F 2250/0013* (2013.01); *A61F 2250/0068* (2013.01); *A61M 2205/332* (2013.01); *A61M 2205/3317* (2013.01); *A61M 2205/3331* (2013.01); *A61M 2205/3344* (2013.01); *A61M 2205/3375* (2013.01)

(58) Field of Classification Search
CPC .. A61M 2205/3331; A61M 2205/3344; A61M 2205/3375; A61M 2205/3317; A61M 2205/332
See application file for complete search history.

(56) References Cited

U.S. PATENT DOCUMENTS

| | | | | |
|---|---|---|---|---|
| 6,129,682 | A * | 10/2000 | Borchert | A61B 5/0066 600/561 |
| 6,186,974 | B1 * | 2/2001 | Allan | A61F 9/00781 604/30 |
| 6,203,513 | B1 * | 3/2001 | Yaron | A61M 27/002 604/9 |
| 6,390,989 | B1 * | 5/2002 | Denninghoff | A61B 3/16 600/561 |
| 6,589,198 | B1 * | 7/2003 | Soltanpour | A61M 5/14586 604/9 |
| 8,246,569 | B1 * | 8/2012 | Meng | A61B 5/4836 604/9 |
| 8,632,489 | B1 * | 1/2014 | Ahmed | A61F 9/00781 604/9 |
| 9,022,968 | B2 * | 5/2015 | Passaglia | A61M 1/77 604/9 |
| 9,125,724 | B2 * | 9/2015 | Berdahl | A61B 3/16 |
| 9,168,172 | B1 * | 10/2015 | Berdahl | A61F 9/00781 |
| 9,498,380 | B2 * | 11/2016 | Berdahl | A61F 9/029 |
| 9,603,742 | B2 * | 3/2017 | Sanchez | A61F 9/00781 |
| 2002/0087111 | A1 * | 7/2002 | Ethier | A61F 9/00781 604/9 |
| 2003/0212383 | A1 * | 11/2003 | Cote | A61F 9/00781 264/171.12 |
| 2004/0193095 | A1 * | 9/2004 | Shadduck | A61F 9/00781 977/944 |
| 2005/0049578 | A1 * | 3/2005 | Tu | A61B 3/16 977/956 |
| 2005/0119737 | A1 * | 6/2005 | Bene | A61F 9/00781 623/4.1 |
| 2005/0125003 | A1 * | 6/2005 | Pinchuk | A61F 9/00781 604/8 |
| 2005/0283108 | A1 * | 12/2005 | Savage | A61F 9/00781 604/8 |
| 2006/0136022 | A1 * | 6/2006 | Wong | A61F 9/0017 607/104 |
| 2007/0073275 | A1 * | 3/2007 | Conston | A61F 9/00781 606/15 |
| 2007/0106199 | A1 * | 5/2007 | Krivoy | A61F 9/00781 604/9 |
| 2007/0118065 | A1 * | 5/2007 | Pinchuk | A61F 9/00781 604/9 |
| 2007/0141116 | A1 * | 6/2007 | Pinchuk | A61F 9/00781 623/6.63 |
| 2007/0185468 | A1 * | 8/2007 | Prywes | A61M 27/006 604/294 |
| 2007/0282282 | A1 * | 12/2007 | Wong | A61N 1/306 604/294 |
| 2007/0282405 | A1 * | 12/2007 | Wong | A61F 7/12 607/104 |
| 2009/0043321 | A1 * | 2/2009 | Conston | A61F 9/00781 606/166 |
| 2009/0275924 | A1 * | 11/2009 | Lattanzio | A61B 3/16 604/9 |
| 2010/0004635 | A1 * | 1/2010 | Lin | A61F 9/00781 216/37 |
| 2010/0161004 | A1 * | 6/2010 | Najafi | A61N 1/3787 607/60 |
| 2010/0249691 | A1 * | 9/2010 | Van Der Mooren | A61F 9/00781 604/9 |
| 2011/0071456 | A1 * | 3/2011 | Rickard | A61B 5/6821 604/9 |
| 2011/0071505 | A1 * | 3/2011 | Rickard | A61B 5/6821 600/398 |
| 2012/0226133 | A1 * | 9/2012 | Wong | A61B 5/6846 600/398 |
| 2012/0302861 | A1 * | 11/2012 | Marshall | A61F 9/00781 600/398 |
| 2013/0085440 | A1 * | 4/2013 | Bohm | A61F 9/00781 604/9 |
| 2013/0096483 | A1 * | 4/2013 | Dacquay | A61F 9/00781 604/9 |
| 2013/0150774 | A1 * | 6/2013 | Field | A61M 1/742 604/9 |
| 2013/0150776 | A1 * | 6/2013 | Bohm | A61F 9/00781 604/9 |
| 2013/0150777 | A1 * | 6/2013 | Bohm | A61F 9/00781 604/9 |
| 2013/0150779 | A1 * | 6/2013 | Field | A61F 9/00781 604/9 |
| 2013/0158381 | A1 * | 6/2013 | Rickard | A61B 3/16 604/8 |
| 2013/0204177 | A1 * | 8/2013 | Field | G06F 16/337 604/9 |
| 2013/0211311 | A1 * | 8/2013 | Field | A61F 9/00781 137/859 |
| 2013/0238015 | A1 * | 9/2013 | Berdahl | A61B 5/6803 606/204.25 |
| 2013/0317412 | A1 * | 11/2013 | Dacquay | A61B 5/03 604/9 |
| 2014/0046439 | A1 * | 2/2014 | Dos Santos | A61F 9/00781 623/6.22 |
| 2014/0171777 | A1 * | 6/2014 | Sanchez | A61B 3/16 600/398 |
| 2014/0172090 | A1 * | 6/2014 | Gunn | A61F 9/00781 623/6.22 |
| 2014/0194834 | A1 * | 7/2014 | Passaglia | A61M 1/77 604/290 |
| 2014/0276343 | A1 * | 9/2014 | Yalamanchili | A61F 9/00781 604/9 |
| 2014/0343476 | A1 * | 11/2014 | Penhasi | A61F 9/00781 604/8 |
| 2014/0364789 | A1 * | 12/2014 | Schaller | A61F 9/00781 427/2.24 |
| 2015/0057523 | A1 * | 2/2015 | Gunn | A61B 3/16 141/2 |
| 2015/0057592 | A1 * | 2/2015 | Gunn | A61F 9/00781 604/9 |
| 2015/0057593 | A1 * | 2/2015 | Johnson | A61F 9/00781 604/9 |
| 2015/0057594 | A1 * | 2/2015 | Gunn | F16K 99/0015 604/9 |
| 2015/0057595 | A1 * | 2/2015 | Gunn | A61F 9/00781 604/9 |
| 2015/0057596 | A1 * | 2/2015 | Lind | A61F 9/00781 604/9 |
| 2015/0057597 | A1 * | 2/2015 | Johnson | A61F 9/00781 604/9 |
| 2015/0164321 | A1 * | 6/2015 | Weibel | A61B 3/16 600/405 |
| 2015/0230982 | A1 * | 8/2015 | Gunn | A61M 5/14276 604/9 |
| 2015/0230983 | A1 * | 8/2015 | Johnson | A61F 9/00781 604/9 |
| 2015/0230984 | A1 * | 8/2015 | Gunn | F04B 19/006 604/9 |

(56) References Cited

U.S. PATENT DOCUMENTS

| | | | |
|---|---|---|---|
| 2015/0257930 A1* | 9/2015 | Lind .................... | A61F 9/00781 604/9 |
| 2015/0257931 A1* | 9/2015 | Sanchez .............. | A61F 9/00781 604/9 |
| 2015/0313761 A1* | 11/2015 | Berdahl ............... | A61B 5/6803 606/204.25 |
| 2016/0058324 A1* | 3/2016 | Cao ..................... | A61B 5/7282 600/302 |
| 2016/0067092 A1* | 3/2016 | Lind ........................ | A61B 3/10 604/8 |
| 2016/0067093 A1* | 3/2016 | Johnson .............. | A61F 9/00781 604/9 |
| 2016/0128587 A1* | 5/2016 | Kuenen ................ | A61B 3/1241 600/561 |
| 2016/0220417 A1* | 8/2016 | Schieber ............. | A61F 9/00781 |
| 2016/0296371 A1* | 10/2016 | Gelvin ................ | A61F 9/00781 |
| 2017/0020730 A1* | 1/2017 | Chew .................. | B29C 45/1671 |
| 2017/0095649 A1* | 4/2017 | Vase ........................ | A61F 7/123 |
| 2020/0030150 A1 | 1/2020 | Oduncu | |

FOREIGN PATENT DOCUMENTS

| | | | | |
|---|---|---|---|---|
| WO | WO-2012136431 A1 * | 10/2012 | ........... | A61B 3/0041 |
| WO | WO-2017035406 A2 * | 3/2017 | ............. | A61B 3/102 |
| WO | 2018174835 A1 | 9/2018 | | |

OTHER PUBLICATIONS

Jonas et al., Association between arterial blood pressure, cerebrospinal fluid pressure and intraocular pressure in the pathophysiology of optic nerve head diseases. In: Clinical and Experimental Ophthalmology, vol. 40, 2012, e233-e234 (2012).

International Search Report of the European Patent Office in PCT/EP2018/071151 (from which this application claims priority) dated Nov. 13, 2018 and English-language translation thereof.

Office Action of the German Patent and Trademark Office dated Apr. 23, 2018 (Priority Application No. DE 10 2017 117 657.8) and English-language translation thereof.

Written Opinion of the European Patent Office in PCT/EP2018/071151 (from which this application claims priority) dated Feb. 7, 2019 and English-language translation thereof.

* cited by examiner

APPARATUS FOR INFLUENCING AN INTRAOCULAR PRESSURE

CROSS REFERENCE TO RELATED APPLICATIONS

This application is a continuation application of international patent application PCT/EP2018/071151, filed Aug. 3, 2018, designating the U.S. and claiming priority to German application 10 2017 117 657.8, filed Aug. 3, 2017, and the entire content of both applications is incorporated herein by reference.

TECHNICAL FIELD

The present disclosure relates to an apparatus for influencing intraocular pressure (IOP).

BACKGROUND

The disclosure is described with reference to glaucoma diseases; however, reference is made to the fact that the apparatus according to the disclosure can also be used in other areas. It is known from the related art that the IOP is important in the case of glaucoma diseases. However, although an elevated IOP is for example an important risk factor in the development of glaucoma, it was recently found that an elevated IOP is not present in all forms of glaucoma. Additionally, even an elevated IOP does not necessarily always increase the risk of developing a disease. In addition to the IOP, the so-called intracranial pressure (ICP) or cerebrospinal fluid (CSF) pressure and, in particular, the ratio of these pressures to the IOP, too, were also found to be important.

Furthermore, in the context of glaucoma therapy, procedures where the IOP is reduced are known from the related art. Thus, the related art has described the use of so-called shunts or stents, for example which allow liquid to be drained from the eye. Glaucoma therapies known from the related art (for example, in the case of narrow-angle and open-angle glaucoma) have hitherto only been based on lowering the IOP or adjusting to statistically determined normal value ranges (e.g., less than 15-20 mmHg). Furthermore, the practice of observing a progression of the glaucoma (normal pressure glaucoma) is also known, for example by determining the decrease in the retinal nerve fiber layer thickness. In these cases, the pressure can only be reduced further, for example to 8-10 mmHg.

Additionally, use is also made of surgical procedures (iridectomies, trabeculectomies) or else the aforementioned implants (shunts or stents) for the purposes of improving natural drainage channels. Trabecular or uveoscleral outflows, in particular, may also be created in the process. Additionally, the creation of completely new drainage channels is also known, for example from the anterior chamber to the suprachoroidal or subconjunctival space, or else to the surface of the eye.

By way of example, unregulated shunts which have a constant flow resistance are known from the related art, and that the pressure drop achieved in each case depends on the current aqueous humor flow and may therefore also fluctuate over the course of the day.

SUMMARY

It is therefore an object of the present disclosure to achieve a normalization or adjustment of eye pressure differences in a more advantageous manner. According to an aspect of the disclosure, the object is achieved by an apparatus for influencing an IOP as described herein.

An apparatus according to an aspect of the disclosure for influencing an IOP includes a controllable discharge device which is configured to discharge a liquid from the eye or from an area of the eye. According to an aspect of the disclosure, the apparatus includes a first sensor device, which captures at least one first value that is characteristic for the IOP of this eye, and a second sensor device, which captures at least one second value that is characteristic for a pressure acting on the eye, and a control device which controls the discharge device taking account of the first value and the second value, Therefore, according to an aspect of the disclosure (at least) two characteristic values are used, which serve to control a corresponding discharge device. Control taking account of the first and the second value is understood to mean that these two values can be used directly or else indirectly, for example by determining a result value that takes these two values into account, such as, as mentioned in more detail below, a difference or a ratio, and this result value is used for control. In particular, the control device controls the discharge device in relation to a flow cross section and/or an amount of the liquid to be discharged from the eye.

Typically, at least one of the two sensor devices has an intracranial arrangement. Typically, at least the first sensor device has an intracranial arrangement. Typically, both sensor devices have an intracranial arrangement. However, at least one of the two sensor devices and, in particular, the second sensor device can have an extracranial arrangement. Typically, the discharge device also has an intracranial arrangement.

By way of example, the pressure difference between the IOP and the ICP can be adjusted or there can be a control on the basis of this pressure difference. The disclosure is therefore also based on the consideration that, if the difference or the ratio deviates from the normal range, it can be assumed that there can be not only mechanical loads on the optic nerve but also deficits in axonal transport, i.e., in the supply to the nerves, which may lead to atrophies or even nerve death.

It is therefore provided that control of the discharge device is precisely also carried out on the basis of two parameters. In a further exemplary embodiment, the apparatus has a limiting device that ensures that a pressure is not lowered below a certain minimum value. In a further exemplary embodiment, the control device is configured to also control the amount and/or the flow cross section of the liquid discharged from the eye. Here, the flow resistance, for example, can be controlled and/or regulated.

Furthermore, according to an aspect of the disclosure, the second characteristic value is characteristic for an intracranial pressure and/or a cerebrospinal pressure. As mentioned above, these two values, in particular, are related. Additionally, a quantity related to these values, such as a dynamic response of the optic nerve, can be determined.

In a further exemplary embodiment, the apparatus includes a processor which determines a result value taking into account the first characteristic value and the second characteristic value, wherein the control device controls the discharge device taking this result value into account. Typically, this result value is used as a controlled variable which, for example, regulates a flow rate of the discharge device. This flow rate, in turn, can be a manipulated variable of the closed-loop control.

Particularly typically, this result value is a difference or a ratio of the first characteristic value and the second characteristic value. In general, the lamina cribrosa separates the two pressurized regions and the pressure drop that occurs across this lamina cribrosa is also referred to as the translaminar pressure difference.

In a further exemplary embodiment, the two sensor devices are arranged separately from one another.

In a further exemplary embodiment, there is a communications link that facilitates data interchange between at least one sensor device and the control device and this communications link is typically selected from a group of communications links containing radio connections, wired connections, sound connections, in particular ultrasound connections, and optical links or light-based communications links. The respective communications signal could be transmitted as a modulated sound signal in an exemplary embodiment. In the case of an optical link, infrared light at a given wavelength could be transmitted through the skull and/or the optic nerve. Additionally, modulated signals via the neural pathways or modulated sound signals or the like would be conceivable.

Different communication links would also be conceivable. In an exemplary embodiment, the first sensor device is configured as a unit with the control device. Typically, this would allow communication links between the first sensor device and the control device to be available as cabled or wired links.

In a further exemplary embodiment, the apparatus includes a processing device for forming differences and/or ratios between the measured measurement values. As mentioned above, the measurement values are in particular pressure measurement values, and the sensor devices typically are in particular pressure sensor devices.

In a further exemplary embodiment, the control device is configured to control the discharge device at least also at times when only taking one of the two measurement values into account. By way of example, the control device could at times control the discharge device only using the measurement value for the IOP. The second characteristic value can be measured at regular, certain intervals and a result or a control can be modified on the basis of this measurement value. Here, the first sensor device, too, can carry out measurements at predetermined time intervals. The first sensor device typically carries out the measurements more frequently than the second sensor device.

Typically, the control device is configured to continuously adapt the pressure difference between the IOP and the ICP. This allows the ICP to be captured continuously or at certain intervals in or at the skull by the second sensor device. As mentioned above, the IOP can be measured in or at the eye using the first sensor device. The signals from these sensor devices, which are typically pressure sensors, are forwarded, processed and, in particular, used for controlling the discharge device which is an IOP-changing (generally lowering) element in this case.

In particular, an adjustable drainage means (shunt) could be provided here to achieve a desired pressure difference between the IOP and the ICP. Here, the discharge device can be embodied in different ways.

Thus, the discharge device can include, for example, a fluid valve that is actuated by osmosis. Such a valve can have an inlet channel for a fluid and an outlet channel which is in flow connection to the inlet channel via an opening. Such a valve is described in US 2014/0172090 A1, for example.

Additionally, a shunt that is introducible into the Schlemm canal could also be provided. This shunt can include a Venturi element in order to determine the liquid flow from an inlet to an outlet. Furthermore, the discharge device typically includes a pump device for suctioning away liquid. In an exemplary embodiment, this pump device can be implantable.

The discharge device may furthermore include a valve element that serves to control a flow of a liquid. Here, the control device can typically also control this valve element. In an exemplary embodiment, the discharge device may also include a capture device for capturing a position of such a valve. A further pump system employable for draining liquid from the eye is described in U.S. Pat. No. 6,589,198 B1, for example.

Furthermore, the drainage device may include elements that regulate the flow of liquids, for instance orifice plates. Thus, an orifice plate with an adjustable orifice diameter could be provided. Orifice plates that are displaceable with respect to one another in order thus to regulate the flow can also be provided.

In a further exemplary embodiment, the discharge device includes a drive device that serves to control a flow. The drive device can be configured as an actuating motor, for example, more generally as an electric motor. In addition, piezo motors or piezo actuators can also be used.

In a further exemplary embodiment, the first sensor device and/or the second sensor device and/or the discharge device includes an electrically operated implant and, in particular, an implant that is inserted or insertable into the eye. Furthermore, a transmitting device and/or a transmitter can be used, which can be placed outside the head, for example. This transmitting device emits an electromagnetic field that is strong enough to supply the implant with electric power. Furthermore, the implant may include a shunt element—in particular, a shunt element that is placeable within the electric field—that likewise is supplied with power by the electric field and can thus be operated.

In a further exemplary embodiment, the discharge device includes a shunt and/or a stent. As a rule, a shunt forms an artificial drainage connection for discharging liquid while a stent is used to modify the flow cross section of a naturally present flow connection.

The apparatus includes a memory device which stores reference values, in particular reference values for the above-mentioned result value, for example a difference between the IOP and the ICP. The controllable discharge device can be actuated accordingly in such a way that a certain setpoint value for this result value, i.e., the difference IOP-ICP, is reached.

In an exemplary embodiment, the sensor devices are configured such that they ascertain at least one change in IOP and/or ICP and typically use this to regulate a controlled variable of the pressure-regulating element or of the outflow device. Here, it is possible, for example, for the control response to be configured as a patient-specifically dynamically learning system, or else as a model-based system for individual and optimal setting of the pressure, for example for minimizing a control error. Thus, for example, a fluctuation in aqueous humor production over the course of a day can be taken into account, in particular in the case of a limited outflow capacity of the outflow device. Thus, for example, the pressure reduction can already be started before there is an increase in the aqueous humor production, which usually takes place in the morning.

In a further exemplary embodiment, the apparatus and in particular the control device includes a memory device which is configured to store measurement and/or operational parameters. In particular, it is possible for personal parameters or factors to be stored, such as the age of the person, gender, environmental factors, and the like. Typically, the processor or the control device controls the outflow device also taking these parameters into account.

Since the effects of inexpedient pressure conditions may also depend on the anatomical conditions (for instance, the thickness of the lamina cribrosa) or else on other personal factors (age, ethnicity, history of disease or therapy, and medication), the option of taking account of these personal factors in the processing unit or the control unit is typically provided. Additionally, further factors or environmental factors may also be taken into account, for instance a time of day, a day-night rhythm and the like.

In a further exemplary embodiment, the control device includes at least one control output for controlling a medicament repository. Typically, the control device also includes a second control output for controlling a second medicament repository.

This means that at least one, and typically two, additional medicament dosages can be controlled. Thus, it is possible, in particular, to also support the pressure conditions by a controlled medicament delivery from medicament repository implants. For example, prostaglandins for improving the outflow of aqueous humor through eye tissue or else beta blockers for dampening the production of aqueous humor in the ciliary body can be released. In this case, the control device is typically configured to take into account a treatment priority order in order to minimize side effects. By way of example, regulation can first be controlled via the drainage device, then prostaglandin can be released and finally beta blockers, too. Here, ICP-changing elements and medicaments could also be used to realize or support the difference between the IOP and the ICP, i.e., the pressure difference setting.

As mentioned above, pressure could be lowered to lower limits, for example 8 mmHg. It would also be possible to first take absolute values of the ICP (CSF) and the IOP in individual measurements and then only detect changes using the sensor devices. The ICP or quantities related to the ICP could also be captured only occasionally (e.g., daily) while the IOP values are determined more frequently, for example every second, minute or hour.

In a further exemplary embodiment, the IOP sensor device, and typically the pressure regulating unit (i.e., the discharge device, in particular), too, is realized in a common module or common unit and typically also operates in the case if the communications link is severed, with the second sensor device.

In a further exemplary embodiment, the apparatus includes a further sensor device which captures measurement values that are characteristic for a position and/or orientation and/or for a movement of the user, i.e., the patient, more particularly the skull of the user. It was found that such quantities may also influence the IOP. Here, this further sensor device may be arranged both intracranially and extracranially. Additionally, further sensor devices that capture values such as, for instance, ambient pressure or temperature may also be provided.

Typically, this further sensor device is selected from a group of sensor devices including inclination sensors, movement sensors, acceleration sensors, and the like. In this case, furthermore, a pausing device can typically be provided, the latter pausing a measurement of the IOP and/or the ICP on the basis of the data output by the further measuring device.

By way of example, an IOP or ICP measurement could be paused in the case of certain inclinations of the head.

By way of example, the head position and/or the acceleration of the body can also be taken into account as these values may have an influence on the pressure conditions in the skull and in the eye. Knowledge of this quantity allows better closed-loop control or an open-loop control of the pressure conditions.

As an alternative to a direct ICP measurement, the dynamics of the optic nerve can also be observed, for example by observing the pulsation of the vessels on the optic nerve head (ONH), and this observation can be used to infer the size of the ICP relative to the IOP and this relation can be used to regulate the pressure. Here, vascular and tissue pulsations can be detected, for example, by optical coherence tomography (OCT), confocal scanners or ultra-sound.

In a further exemplary embodiment, the apparatus includes a power storage device, which supplies at least one of the aforementioned units and in particular the discharge device with electric power. Here, the power storage can be a power storage that obtains its energy from an electrolyte and/or an at least partly endogenous substance. However, as mentioned above, power sources that provide the sensor device and/or the discharge device with power from the outside may also be provided.

In a further exemplary embodiment, the control device is embodied as a relay station and/or an external communications interface. The latter can typically output control commands to the discharge device.

In a further exemplary embodiment, the control device is configured to enable bidirectional (data) communication with at least one sensor device and typically with both sensor devices. The control device is typically also configured to enable bidirectional (data) communication with the discharge device. Firstly, control commands can be output from the control device to the discharge device. Conversely, data can typically also be output from the discharge device to the control device, such as for example data which are characteristic for a position of valves or the like.

In a further exemplary embodiment, the control device may also include a timer device. In this way, for instance, a clocking of the individual values measured by the sensor devices can be controlled. In general, the control device can be configured to output commands to the sensor devices, said commands each causing measurements to be carried out by the sensor devices.

In particular, this may implement a measurement data transfer from the sensor device or devices to the control device. Conversely, data and/or commands can typically also be transferred from the control device to the sensor devices.

Furthermore, the present disclosure is directed to a method for influencing IOP. Here, a liquid is discharged at least at times from at least one area of the eye by a controllable discharge device.

According to an aspect of the disclosure, a first sensor device is used to capture at least at times one first value that is characteristic for the IOP (of the eye), and a second sensor device is used to capture at least one second value that is characteristic for a pressure acting on the eye. Furthermore, a control device controls the discharge device at least at times taking account of the first characteristic value and the second characteristic value.

In a further exemplary method, at least one sensor device and in particular the second sensor device communicates wirelessly with the control device. In a further exemplary method, at least one of the characteristic values is a pressure value.

The first sensor device and the second sensor device measure the characteristic values at predetermined time intervals. These time intervals differ from one another. Typically, the second sensor device measures the second measured value at longer time intervals and/or less frequently than the first sensor device.

In a further exemplary method, the control device controls at least one medicament release. Particularly typically, the control device controls the medicament release also on the basis of at least one of the two measured measurement values.

BRIEF DESCRIPTION OF THE DRAWINGS

The disclosure will now be described with reference to the drawings wherein.

DESCRIPTION OF EXEMPLARY EMBODIMENTS

Figure 1:
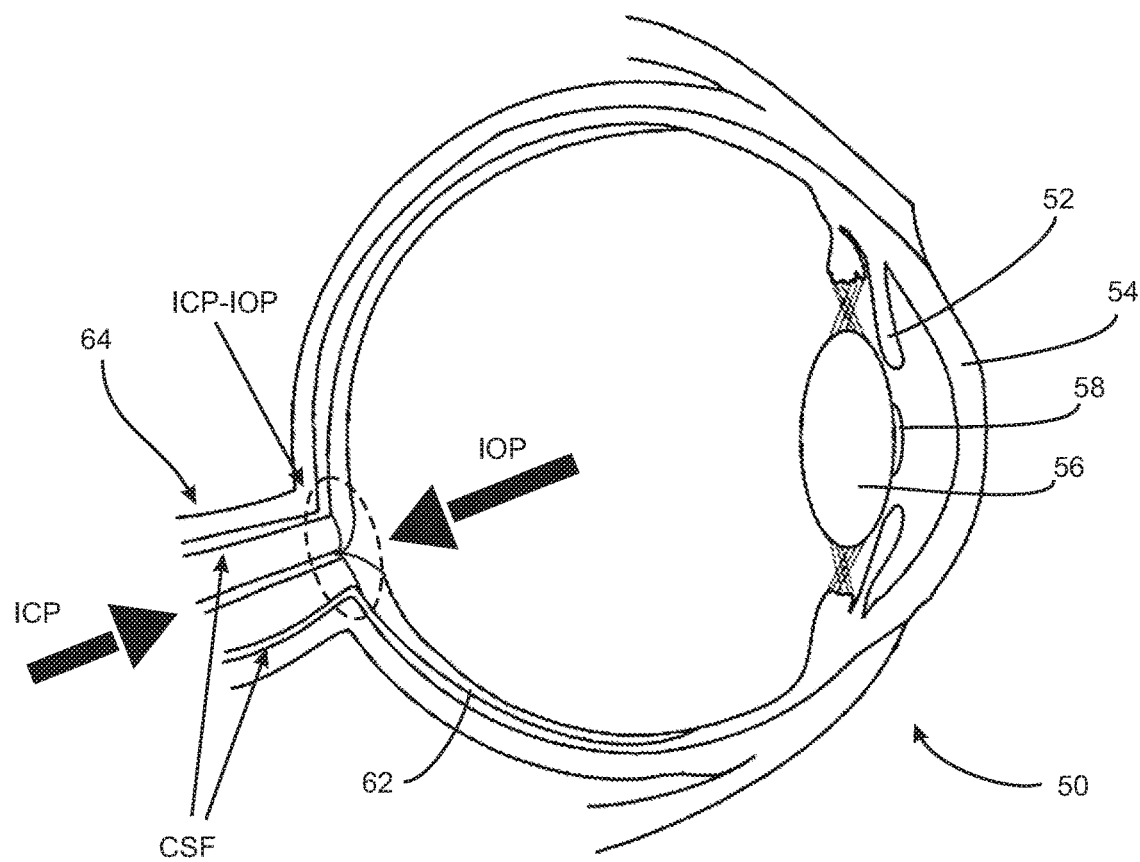
FIG. 1 shows a representation of a human eye for visualizing the object according to an exemplary embodiment the disclosure.

FIG. 1 shows a schematic representation of a human eye 50. Here, reference sign 52 refers to the iris of the eye and reference sign 54 refers to the cornea. Reference sign 56 denotes the lens and reference sign 58 denotes the pupil. Reference sign 62 denotes the retina of the eye and reference sign 64 denotes the optic nerve. As indicated by the arrow IOP, the IOP here acts from the eyeball outwards. Furthermore, as shown by the second arrow ICP, the cerebrospinal pressure also acts inwards. The pressure difference ICP-IOP occurs in the zone marked with dashed lines. This is a particularly relevant measurement value. The reference sign CSF refers to the cerebrospinal fluid. It is known to remove eye fluid by discharge devices (not shown in FIG. 1), such that in particular the IOP is reduced.

Figure 2:
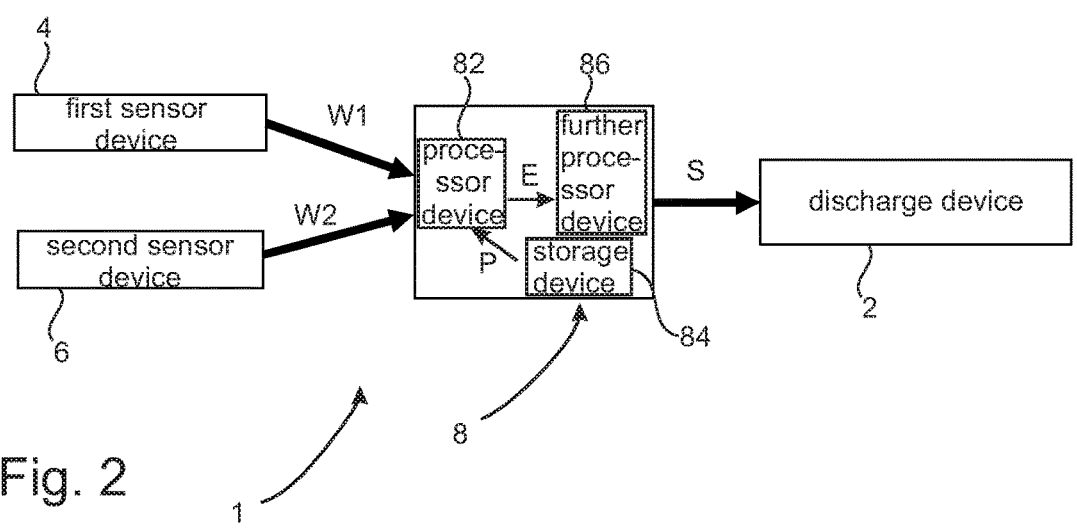
FIG. 2 shows a block diagram of an apparatus according to a first exemplary embodiment of the disclosure.

FIG. 2 shows a block diagram of an apparatus according to a first exemplary embodiment of the disclosure. This apparatus 1 includes a discharge device 2 which is controllable, and which serves to discharge liquid from the eye 50. Here, this discharge device 2 is controllable and typically regulable, wherein, in particular, a flow rate of the liquid to be discharged from the eye 50 is regulable.

Reference sign 8 denotes a control device which is configured to control or regulate the discharge device 2. Here, the control device 8 can regulate, in particular, the flow rate caused by the discharge device 2.

Reference sign 4 denotes a first sensor device which captures a measurement value W1 that is characteristic for the IOP and outputs said measurement value to the control device 8. Reference sign 6 denotes a second sensor device which outputs a measurement value W2 to the control device 8, wherein, as mentioned above, said measurement value W2 is a value for an intracranial pressure and/or a cerebrospinal pressure.

As indicated by the arrows at W1 and W2, these measurement values W1 and W2 are made available to the control device 8. Reference sign 82 denotes a processor which serves to determine a result value E from these two values W1 and W2, in particular by a mathematical operation. By way of example, this result value E can be a difference between the two values W1 and W2, i.e., for example, a difference between the ICP and the IOP.

Reference sign 84 denotes a storage device which likewise is or can be a constituent part of the control device 8 and in which, for example, person-specific data can be stored. A further processor 86 determines a manipulated variable S from the result value E, which manipulated variable is fed to the discharge device 2 such that, in particular, the latter controls a flow of eye fluid accordingly.

As mentioned above, the control device 8 and the discharge device 2 can be embodied as a common module, for example. Furthermore, the first sensor device 4 and the control device 8 can also be embodied as a common module. The first sensor device 4 and the discharge device 2 can also be embodied as a common module. Furthermore, the first sensor device 4, the control device 8 and the discharge device 2 can also be realized as a common module.

Figure 3:
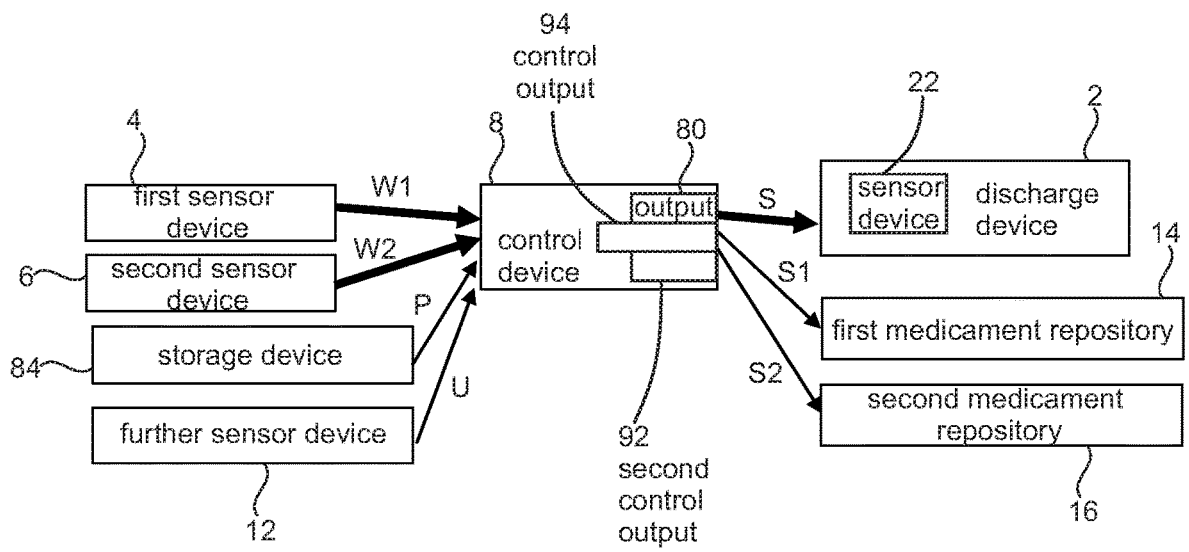
FIG. 3 shows a block diagram of an apparatus according to a second exemplary embodiment of the disclosure.

FIG. 3 shows a further block diagram of an apparatus according to a second exemplary embodiment of the disclosure. Here too, the first sensor device 4 and the second sensor device 6 are illustrated again, said sensor devices transmitting the respective values W1 and W2 to the control device 8. Additionally, a further sensor device 12 is provided which transfers ambient values U to the control device 8. By way of example, these ambient values can be acceleration values, inclination values and the like, i.e., in particular, values that characterize movements or orientations of the user whose eye pressure should be corrected. The storage device 84, too, can also transfer values P, i.e., personal values of the user, to the control device 8, for instance, as mentioned above, values that characterize the age of the user, an ethnicity or history of disease or previous histories. The control device 8 and, more precisely, the processor 82 (not shown), for example, process these values and control the discharge device 2 by a manipulated variable S via an output 80, also on the basis of these values. The discharge device 2 in turn may include a sensor device 22, which measures the manipulated variable or position of the discharge device 2 (in particular an actuating element of this discharge device) and which, where necessary, returns these values to the control device 8, too, for regulating purposes.

Reference sign 94 denotes a control output of the control device 8, via which control output, for example, a signal S1 can be output to a first medicament repository 14. Reference sign 92 denotes a second control output, via which, for example, a signal S2 can be output to a second medicament repository 16. On the basis of these signals, these medicament repositories can release medicaments to the user, particularly in a predetermined manner.

Figure 4:
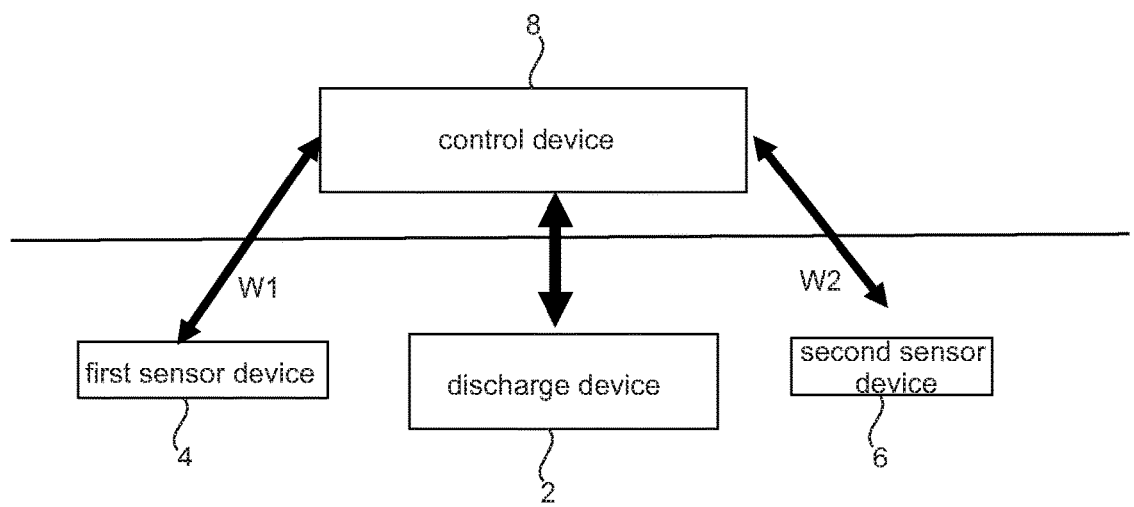
FIG. 4 shows a block diagram of an apparatus according to an alternative exemplary embodiment of the disclosure.

FIG. 4 shows an apparatus according to a further exemplary embodiment of the disclosure. In this exemplary embodiment, an external communication interface or control device 8 is provided. The latter is arranged, in particular, outside the user's head (extracranially), for instance in a spectacle temple or in an head-mounted device (HMD). Here, provision is made, in particular, for the control device 8 to implement bidirectional communication both with the sensor devices 4 and 6 and with the discharge device 2. The sensor devices 4 and 6 and also the discharge device 2 are provided intracranially here, i.e., within the head.

Pressure control for the discharge device 2 is implemented here, in turn, by the control device 8. Conversely, status information can be transmitted from the discharge device 2 to the control device 8 via the bidirectional connection.

Furthermore, certain values could also be measured non-invasively or from outside the skull. By way of example, use can be made of an apparatus that is based on the principle that the ICP correlates directly with a pressure within the central retinal vein in the eye.

The applicant reserves the right to claim as essential to the disclosure all of the features that are disclosed in the application documents, provided they are novel over the related art, either individually or in combination. It should also be noted that features that may be advantageous per se have also been described in the individual figures. A person skilled in the art will immediately see that a particular feature described in a figure can also be advantageous without the adoption of further features from this figure. Furthermore, a person skilled in the art will see that advantages can also be afforded by a combination of several features shown in individual figures or in different figures.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 First embodiment of an apparatus according to the disclosure
2 Discharge device
4 First sensor device
6 Second sensor device
8 Control device
12 Further sensor device
14 First medicament repository
16 Second medicament repository
22 Sensor device of the discharge device
50 Human eye
52 Iris
54 Cornea
56 Lens
58 Pupil
62 Retina
64 Optic nerve
80 Output
82 Processor
84 Storage device
86 Further processor
92 Second control output
94 Control output
E Result value
IOP Intraocular pressure
P Values
S Manipulated variable
S1 Signal
S2 Signal
U Ambient values
W1 Measurement value
W2 Measurement value
CSF Cerebrospinal fluid
ICP Intracranial pressure

What is claimed is:

1. An apparatus for influencing an intraocular pressure (IOP) of an eye, the apparatus comprising:
a controllable discharge device configured to discharge a liquid from at least one area of the eye;
a first sensor device which captures at least one first characteristic value characteristic for the IOP;
a second sensor device which captures at least one second characteristic value characteristic for a pressure acting on the eye;
a control device configured to control the controllable discharge device at least at times taking account of the at least one first characteristic value and the at least one second characteristic value;
a further sensor device which captures measurement values that are characteristic for a position or orientation of a person's body or of parts of the person's body;
the at least one second characteristic value being characteristic for an intracranial pressure;
the control device being configured to control a flow cross section of the liquid discharged from the eye; and/or
the control device being configured such that a flow resistance is controlled and/or regulated; and
a processor configured to determine a result value taking into account the at least one first characteristic value and the at least one second characteristic value,
wherein the control device is further configured to control the controllable discharge device based on the result value,
wherein the control device is further configured to control the controllable discharge device at least at times only based on one of two measurement values, wherein the two measurement values are the first characteristic value and the second characteristic value,
wherein the result value is a difference or a ratio of the at least one first characteristic value and the at least one second characteristic value,
wherein the apparatus is configured such that the first sensor device captures the first characteristic value at predetermined time intervals, and
wherein the first sensor device captures the first characteristic value more frequently than the second sensor device.

2. The apparatus as claimed in claim 1, further comprising:
a communications link between at least one sensor device and the control device; and
the communications link being selected from a group of communications links including radio connections, wired connections, sound connections, ultrasound connections, or light-based communications links.

3. The apparatus as claimed in claim 1, wherein the control device includes a memory device configured to store operational parameters.

4. The apparatus as claimed in claim 1, wherein the control device includes at least one control output for controlling a medicament repository.

5. The apparatus as claimed in claim 1, wherein the controllable discharge device includes a shunt and/or a stent.

6. The apparatus as claimed in claim 1, wherein the control device is configured to control the discharge device at times only using the first characteristic value for the IOP, and
wherein the apparatus is configured such that the second characteristic value is measured at regular intervals and a control of the discharge device is modified based on the second characteristic value.

7. The apparatus as claimed in claim 1, wherein the control device is configured to continuously adapt a pressure difference between the intraocular pressure (IOP) and the intracranial pressure.

8. The apparatus as claimed in claim 1, wherein an adjustable drainage means is provided to achieve a desired pressure difference between the IOP and the ICP.

9. The apparatus as claimed in claim 1, wherein the discharge device is an IOP-changing element.

10. The apparatus as claimed in claim 1, wherein the apparatus has a limiting device that ensures that a pressure is not lowered below a certain minimum value.

11. The apparatus as claimed in claim 1, wherein the sensor devices are configured such that they ascertain at least one change in IOP and/or ICP and use this change to regulate a controlled variable of a pressure-regulating element or of an outflow device.

12. The apparatus as claimed in claim 11, wherein a control response is configured as a patient-specifically dynamically learning system.

13. The apparatus as claimed in claim 11, wherein a control response is configured as a model-based system for individual and optimal setting of the pressure.

14. An apparatus for influencing an intraocular pressure (IOP) of an eye, the apparatus comprising:
    a controllable discharge device configured to discharge a liquid from at least one area of the eye;
    a first sensor device which captures at least one first characteristic value characteristic for the IOP;
    a second sensor device which captures at least one second characteristic value characteristic for a pressure acting on the eye;
    a control device which is implantable and configured to control the controllable discharge device at least at times taking account of the at least one first characteristic value and the at least one second characteristic value;
    a further sensor device which captures measurement values that are characteristic for a position or orientation of a person's body or of parts of the person's body;
    the at least one second characteristic value being characteristic for an intracranial pressure;
    the control device being configured to control a flow cross section of the liquid discharged from the eye; and/or
    the control device being configured such that a flow resistance is controlled and/or regulated; and
    a processor configured to determine a result value taking into account the at least one first characteristic value and the at least one second characteristic value,
    wherein the control device is further configured to control the controllable discharge device based on the result value,
    wherein the control device is further configured to control the controllable discharge device at least at times only based on one of two measurement values, wherein the two measurement values are the first characteristic value and the second characteristic value,
    wherein the result value is a difference or a ratio of the at least one first characteristic value and the at least one second characteristic value,
    wherein the apparatus is configured such that the first sensor device captures the first characteristic value at predetermined time intervals, and
    wherein the first sensor device captures the first characteristic value more frequently than the second sensor device.

* * * * *